United States Patent [19]

Rumpf

[11] 4,089,949

[45] May 16, 1978

[54] INJECTABLE THERAPEUTIC COMPOSITIONS

[76] Inventor: Karl Rumpf, 3006 Grossburgwedel, Entenfang 22, Germany

[21] Appl. No.: 677,801

[22] Filed: Apr. 16, 1976

Related U.S. Application Data

[63] Continuation of Ser. No. 508,574, Sep. 23, 1974, abandoned.

[30] Foreign Application Priority Data

Sep. 24, 1973 United Kingdom .............. 44679/73

[51] Int. Cl.² .................. A61K 31/505; A61K 31/625
[52] U.S. Cl. ..................................... 424/229; 424/251
[58] Field of Search ............................... 424/229, 251

[56] References Cited

U.S. PATENT DOCUMENTS

| | | | |
|---|---|---|---|
| 2,895,874 | 7/1959 | Lux et al. ............................... | 424/229 |
| 3,507,952 | 4/1970 | Rednick et al. .................. | 424/229 X |
| 3,551,564 | 12/1970 | Kläui et al. ........................... | 424/229 |
| 3,985,873 | 10/1976 | Alvan et al. .......................... | 424/177 |
| 3,985,876 | 10/1976 | Hazlett et al. ........................ | 424/229 |

*Primary Examiner*—Allen J. Robinson
*Attorney, Agent, or Firm*—Donald Brown

[57] ABSTRACT

An injectable synergistic one-phase formulation, which comprises a potentiated composition consisting of sulphadimidine, sulphathiazole and trimethoprim dissolved in aqueous N,N-dimethylacetamide, wherein the X% w/v concentration is from 10 to 50% w/v, the ratio of sulphadimidine to sulphathiazole is from 0.3 to 3, the ratio of the sulphonamides together to trimethoprim from 3.5 to 7, and the water content of the N,N-dimethylacetamide is less than (50-X)% v/v, methods for the preparation of such a formulation and for the use of the same for the treatment of animals.

7 Claims, No Drawings

INJECTABLE THERAPEUTIC COMPOSITIONS

This is a continuation of application Ser. No. 508,574 filed Sept. 23, 1974, now abandoned.

The present invention relates to injectable therapeutic compositions containing sulphonamides and a sulphonamide potentiator.

It is well known that the chemotherapeutic, especially antibacterial activities of sulphonamides and of certain 2,4-diamino-pyrimidine derivatives, are mutually enhanced when these agents act together in the human or animal organism. Trimethoprim is now well established as one of the best potentiators of sulphonamides in human and veterinary medicines, and has widely been used in combination with sulphamethoxazole, sulphadiazine and sulphadoxine.

Whilst such preparations are frequently administered orally, there is also a need for injectable formulations which are sufficiently concentrated for convenient use and are highly active against various infections. This problem of the size of the injectable solution containing an effective dosage of the potentiated combination, is particularly important when the treatment of large domestic animals arises in veterinary practice.

It is not possible to keep both the sulphonamide and the trimethoprim components in aqueous solution simultaneously since the former provides soluble salts only with certain bases whilst the basically reacting potentiators give suitable soluble salts only with certain acids. The mixing of such aqueous solutions of the components inevitably results in precipitation, which makes manufacture of injectable solutions in this manner impossible.

Various attempts have been made to overcome the difficulties and formulate these medicaments for injection. According to British patent specification No. 1,176,395 (or DOS No. 1,617,521), the sulphonamide is prepared in an aqueous solution as a salt and the potentiator in a water-miscible organic solvent before the two solutions are combined. The use of the alkali metal salts represents highly basic conditions, but when the pH is adjusted to provide milder conditions insoluble complexes of the sulphonamide, e.g. sulphamethoxazole with trimethoprim, are formed. In addition, any provision of concentrations substantially higher than 20%, requires the increase of the sulphonamide relative to the potentiator, which results in a medically less advantageous formulation.

Highly concentrated aqueous systems, which could nevertheless maintain the often optimum 5 to 1 ratio of these two types of components, were suggested according to the specification of British patent application No. 12,348/70 or DEP No. 2,112,049. The preparations of such systems involved the use of a finely dispersed suspension of the potentiator in an alkaline solution of the sulphonamide. Although this represents a satisfactory preparation for the purpose of treatment in many cases, the two-phase character of the formulation constitutes a departure from the ideal of a clear solution, which is preferred for injection in many instances and is essential for intravenous administration.

It has now been found that a one-phase formulation of a combination of trimethoprim with two selected sulphonamides, namely sulphadimidine and sulphathiazole, can be achieved at a high concentration without resorting to any use of inorganic salt-forming agents. The solvent required for this purpose is a system consisting of N,N-dimethylacetamide and water in a specified proportion which depends on the total concentration of the potentiated medicament combination, incorporated in the formulation. In this manner the complete omission of solubilising, stabilising nd preservative agents, often required to prevent crystallisation or decomposition of the ingredients at normal or low temperatures, can be achieved. Under the conditions specified according to the invention, the concentration of the active ingredients can be above 40% or even higher without the necessity of distorting the optimum ratios of the potentiator to the sulphonamide, or rendering the physical properties of the solution unsuitable for injections.

According to the present invention in one aspect therefore there is provided an injectable one-phase formulation, which comprises a potentiated composition consisting of sulphadimidine, sulphathiazole and trimethoprim dissolved in aqueous N,N-dimethylacetamide, wherein the X% w/v concentration of the composition is from 10 to 50% w/v, the ratio of sulphadimidine to sulphathiazole is from 0.3 to 3, preferably around 1, the ratio of the sulphonamides together to trimethoprim from 3.5 to 7, preferably around 5, and the water content of the N,N-dimethylacetamide is less than $(50-X)\%$ v/v, preferably at least $0.3(50-X)\%$ v/v.

In view of the fact that the solvent so defined has a specific gravity in the pure form from 0.934 to 1.00g/cm$^3$, the total w/v% of the active ingredients together with a water content is less than 50% w/v and could take a minimum value around 44% w/v.

Since the formulation according to the invention is using the components in their free form as weak acids and bases, respectively, the overall reaction of the solution can be assumed to be neutral relative to the body fluids of the injected species. In the absence of substantial excesses of alkaline salt-forming agents characteristic of prior formulations, trimethoprim may more readily be absorbed from the site of injection than before. No undesirable or abnormal side effects or local reactions were observed in use, and the formulation was found safe and efficacious for the treatment of animals suffering from a variety of bacterial infections. The small size of the vaccine, around 20 ml. for 400 to 600 Kg. body weight, is particularly convenient when horses are injected intramascularly in view of the well known sensitivity of these animals to intramuscular treatment.

The trimethoprim component can be advantageously prepared for incorporation in the formulations according to the present invention by reacting guanidine with a compound of general formula (I)

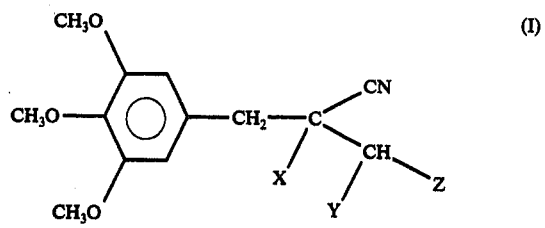

When X and Y taken together represent an additional bond, Z represents either:
(i) the group NR$^4$R$^5$ which is an aliphatic, heterocyclic, or aromatic amino group, preferably an anilino or morpholino group, wherein R$^4$ and R$^5$ cannot both be hydrogen, suitable process conditions for the reaction with guanidine being those described in Belgian Pat. No. 746,846 or U.S. patent application Ser. No. 16606 filed Mar. 4, 1970, now U.S. Pat. No. 3,697,512; or (ii) an alkoxy, preferably a methoxy, or thioalkyl group, suitable process conditions for the reaction with guanidine being those described in, for example, United Kingdom patent specification No. 957,797.

When X represents a hydrogen atom Y and Z each represent an alkoxy group, preferably a methoxy group, or taken together represent an alkylene dioxy group. That is, when X represents a hydrogen atom, the —CHYZ moiety represents a dialkyl or an alkylene acetal group, preferably a dimethyl acetal group. It will be appreciated that the dialkyl acetal group has an acyclic structure while the alkylene acetal group has a cyclic structure. Suitable process conditions for the reaction with guanidine being those described in, for example, United Kingdom patent specification Nos. 1,142,654 or 1,102,142.

The reaction with guanidine may be conveniently effected in a lower alkanol solvent, for example, methanol, ethanol or isopropanol, at elevated temperatures. It is particularly preferred that the reaction be carried out at the reflux temperature of the reaction mixture but useful reaction rates have been obtained at temperatures down to room temperature. It has been found that the reaction with guanidine of compounds of formula (II) wherein X and Y together represent an additional bond and Z represents the group $NR^4R^5$ can also be effected if the quanidine is in the form of the carbonate in a polar aprotic solvent, e.g., dimethyl sulphoxide or hexamethyl phosphoramide. The guanidine is, however, normally utilized in the form of the salt of a strong acid, such as the hydrochloride, in the presence of at least an equivalent of a base sufficient to liberate the guanidine.

The trimethoprim prepared in this manner may then be isolated, and purified, if necessary, for incorporation in the injectable formulation.

The use of a combination of two sulphonamides contributes to the stability of the solution, and is also advantageous from the clinical point of view. The antibacterial efficacy of the equimolar mixtures of sulphadimidine and sulphathiazole is superior to that of sulphadiazine in many instances, and the solubilities of these agents are higher than that of sulphadiazine both in acid and alkaline media. This is important from the point of view of kidney compatibility and is advantageous when the product is administered to newly born piglets or patients with kidney damage.

The relative proportions of the sulphadimidine and sulphathiazole can be varied as suggested above, although it is preferred to use them in about equal amounts. The ratio of the sulpha-components to trimethoprim may also be adjusted within the suggested limits to suit the requirements of the treated animals and the nature of the disease. It appears that a 5 to 1 ratio is clinically optimum and convenient in many instances.

Formulations according to the invention can be easily prepared by dissolving for instance first the sulpha-components in the aqueous solvent mixture having the appropriate water content, and adding trimethoprim afterwards. For certain purposes N,N-diethylacetamide can replace partially or fully the required adjusted N,N-dimethylacetamide without any appreciable difference. The volume of the formulation may be finally adjusted by the addition of further amounts of acetamide or small amounts of other non-aqueous solvents. The amounts of the potentiated composition can conveniently vary within the formulation from 10 to 50%, preferably from 20 to 48% w/v. For larger animals the concentration may be adjusted to say 48%, whilst middle size animals or calves are preferably injected with 24% solutions. The composition may also contain other ingredients, such as anti-histamines, vitamins or corticosteroids.

Effective dosages for the treatment of cattle or horses may conveniently contain 1.6g. of trimethoprim and 8.0g. of equimolar sulphadimidine and sulphathiazole in a 20ml. solution. More diluted versions containing 2.4g. of total ingredients in 10ml. are recommended for middle-size animals, such as pigs or calves, and smaller dosages of the same formulation 1ml, may be eminently suitable for small domestic animals.

The bulk of the solution prepared on a large scale may be easily sterilised by filtration for instance through Seitz-filters, (e.g. 10-2 type in K 7 layers) under pressure. The solution so obtained can be distributed into sterile ampoules as required.

According to the present invention in another aspect, there is provided a method for the treatment of animals and human patients, which comprises the administration of an effective dosage of a formulation, as hereinbefore defined. In particular from 16mg./Kg. to 24mg./Kg, preferably around 20mg./Kg, can be administered by the intramuscular or intravenous route.

EXAMPLE 1

Aqueous N,N-dimethylacetamide (7.5 liters), containing 20% v/v water, was transferred into a 10-liter flask and allowed to stand for 10 minutes under a stream of nitrogen gas. Sulphadimidine (1kg) was added at room temperature (20° C) into the solvent and dissolved whilst continuing the introduction of nitrogen gas flow. As soon as clear solution was achieved sulphathiazole (1kg) was introduced and brought into solution under similar conditions at room temperature before trimethoprim (400g) was added in the same manner.

The completed solution containing all three active ingredients was adjusted to the required final volume (10 liters) with N,N-dimethylacetamide containing 20% v/v water.

A sterile 10-liters Seitz-filter was gased with nitrogen and rinsed with 200ml of aqueous N,N-dimethylacetamide. The solvent was rejected and the above prepared 24% w/v solution was filtered under nitrogen pressure (0.8 ata.) into a sterile, dry, gassed flask.

The solution so obtained was then distributed into sterile 100 ml-flasks and was ready for use. Light was excluded from all these operations in view of the sensitivity of the product. The formulation was tested by injecting calves and pigs intramuscularly and intravenously in dosages of 10 ml. (per 100–150 Kg. body weight), with satisfactory results.

What we claim is:

1. An injectable aqueous one-phase formulation for treating bacterial infections in animals and humans, which comprises x% w/v of a potentiated composition consisting of sulphadimidine, sulphathiazole and trimethoprim dissolved in aqueous N,N-dimethylacetamide, wherein the x% w/v concentration of the composition is from 10 to 50% w/v, the ratio of sulphadimidine to sulphathiazole is from 3:1 to 1:3, the ratio of the sulphonamide together to trimethoprim is from 3.5:1 to 7:1, and the water content of the N,N-dimethylacetamide is less than $(50-x)\%$ v/v and at least $0.3 \times (50-x)\%$ v/v.

2. A formulation according to claim 1, wherein the ratio of sulphadimidine to sulphathiazole is around 1:1.

3. A formulation according to claim 1, wherein the ratio of sulphonamides together to trimethoprim is around 5:1.

4. A formulation according to claim 1, wherein the total concentration of therapeutically active ingredients is 24% w/v.

5. A method of treating bacterial infections in animals and humans having a bacterial infection comprising the intramuscular or intravenous administration to said animal or human of an effective antibacterial dosage of a formulation, as defined in claim 1.

6. A method according to claim 5, wherein the dosage is 16 to 24 mg/kg.

7. A method according to claim 5, wherein 10 ml of a 24% w/v formulation is injected intramuscularly or intravenously into calves and pigs.

* * * * *